United States Patent [19]

Sjödin

[11] Patent Number: 5,164,589

[45] Date of Patent: Nov. 17, 1992

[54] REUSABLE OPTICAL INTERFACE FOR NON-PERMANENT PASSIVE LIGHT COUPLING

[75] Inventor: Håkan Sjödin, Uppsala, Sweden

[73] Assignee: Pharmacia Biosensor AB, Uppsala, Sweden

[21] Appl. No.: 681,532

[22] PCT Filed: Nov. 9, 1989

[86] PCT No.: PCT/SE89/00645

§ 371 Date: May 10, 1991

§ 102(e) Date: May 10, 1991

[87] PCT Pub. No.: WO90/05317

PCT Pub. Date: May 17, 1990

[30] Foreign Application Priority Data

Nov. 10, 1988 [SE] Sweden .................. 8804075

[51] Int. Cl.$^5$ .................. G01N 21/55; G01N 21/63
[52] U.S. Cl. .................. 250/227.24; 356/244
[58] Field of Search ............ 250/227.24; 356/445, 356/71, 244; 385/54, 58

[56] References Cited

U.S. PATENT DOCUMENTS

| 3,865,488 | 2/1975 | Del Rio | 356/71 |
| 3,910,678 | 10/1975 | McCartney et al. | 385/58 |
| 3,963,323 | 6/1976 | Arnold | 385/54 |
| 4,120,585 | 10/1978 | De Palma et al. | 356/71 |
| 4,385,831 | 5/1983 | Ruell | 356/71 |
| 4,428,670 | 1/1984 | Ruell et al. | 356/71 |
| 4,544,267 | 10/1985 | Schiller | 356/71 |
| 4,569,080 | 2/1986 | Schiller | 356/71 |
| 4,747,652 | 5/1988 | Campbell et al. | 350/96.15 |
| 4,759,605 | 7/1988 | Shen et al. | 350/96.15 |
| 4,844,613 | 7/1989 | Batchelder et al. | 356/445 |

FOREIGN PATENT DOCUMENTS

| 0147363 | 7/1985 | European Pat. Off. |
| 0409293 | 1/1991 | European Pat. Off. |
| 2148024A | 5/1985 | United Kingdom | 356/244 |

*Primary Examiner*—David C. Nelms
*Assistant Examiner*—S. Allen

[57] ABSTRACT

An optical interface means for non-permanent passive coupling of light between two optically transparent media comprises a support member (3), and at least one shaped body (6) of an optically transparent elastic material supported thereby and adapted to resiliently contact said solid medium or media, said elastic material having a matching refractive index in respect of said media.

8 Claims, 3 Drawing Sheets

REUSABLE OPTICAL INTERFACE FOR NON-PERMANENT PASSIVE LIGHT COUPLING

The present invention relates to a novel means for coupling light between two light transmitting media, and more particularly to a reusable solid type means for non-permanent light coupling.

The conventional way of making a non-permanent passive (i.e. not refracting or diffracting) light coupling between two light transmitting elements consists in sealingly connecting the two elements by an immersion oil, or in some applications, an uncured silicone rubber composition, having a suitable refractive index. This requires an accurate amount of the coupling medium to be dispensed, making necessary either manual handling or mechanical equipment. The immersion oil must also be removed from one or both elements for each new coupling operation to obtain a good light coupling without disturbing air bubbles. Such removal of the immersion oil by wiping it off or other cleaning is also a messy and time-consuming procedure which in addition to involving the risk of scratching the optical surfaces is difficult to automate in, for example, a commercial measuring instrument. Furthermore, the oil may easily contaminate or smear instrument parts, optical details and sensing surfaces which, of course, is a considerable inconvenience particularly in commercial type apparatuses.

One object of the present invention is to provide an improved passive light coupling means devoid of the above mentioned and other disadvantages and deficiencies of the prior art non-permanent light coupling means, preferably for use in an optical imaging system.

Another object of the invention is to provide a reusable passive light coupling means having a matching refractive index with regard to at least one of the media between which it is to couple light to ensure low refractive index losses, substantially no light refraction or diffraction, and low scattering of light, and which will maintain the polarization directions of the light.

Still another object of the invention is to provide a passive light coupling means which is reusable, i.e. that may be repeatedly connected or "docked" to the same or other solid light transmitting media, but which may be replaced in case of contamination or if otherwise made unusable.

The above mentioned and other objects are achieved by a reusable optical solid type interface means for nonpermanent passive coupling of light between two light transmitting media, such as between a solid optically transparent medium, e.g. a glass prism, and another optical medium, e.g. glass, water or air.

In one embodiment the optical interface means (hereinafter sometimes simply called "optointerface") of the invention comprises a support member, and one or more (shaped) members of an optically transparent elastic or resilient material supported by said support member and adapted to contact at least one of said light transmitting media and having a matching refractive index with respect thereto.

The support means may merely provide a frame for the elastic material body or bodies, the latter being suspended therein, in which case the support means need not be transparent, or the elastic material body or bodies may be attached to one or both faces of a transparent support means, such as a transparent plate or disk, or a lens or prism. In the latter case the transparent elastic material should, of course, have a matching refractive index also with regard to the support means. Particularly in the last-mentioned case the support means may preferably be provided with a holder or the like to facilitate the handling of the unit.

The term "matching refractive index" used herein is a relative one and means that the refractive index of the elastic material should be appropriately matched or adapted to the contacting media in accordance with each particular application. For instance, in case the incident light is normal to a planar interfacial contact surface between the light coupling means and the solid medium or media, rather "extensive" differences between the refractive indices of the respective material may be tolerated, whereas only moderate or small refractive index deviations may be allowed in case of applications with obliquely incident light.

The contact face or faces of the elastic material body or bodies should preferably be shaped to prevent to the outmost extent the enclosure of air-bubbles. The optimum contact surface shape or configuration will, or course, depend on the particular application, and may, for example, be domeshaped or stepped.

The optically transparent elastic material may be any material meeting the specific requirements concerning elasticity, strength, refractive index, etc., for each particular application, and to find suitable materials for a particular application, in view of the disclosure herein, is within the skill of a person skilled in the art. As examples of broad material classes may be mentioned transparent rubber or (cross-linked) elastomers, such as silicone rubber or polybutadiene; and transparent epoxy resins.

The present inventive concept may be applied to all conceivable situations, applicances or apparatus where a non-permanent passive light coupling is to be accomplished. Exemplary is light coupling for all measuring principals based upon "internal reflection" where the reflecting surface is to be separable from a stationary light coupling glass body, such as in measuring of ATR (Attenuated Total Reflection), e.g. SPR-technique (surface plasmon resonance); Brewster angle reflectometry and evanescent wave ellipsometry; and of IRS (Internal Reflection Spectroscopy), e.g. internal reflection infrared spectroscopy, internal reflection fluorescence or total internal reflection fluorescence. Other contemplated applications for the coupling or optical interface means of the present invention are:

As a prism coupler for refractive index measurements on planar substrates;

For light coupling to/from light-wave guiding units for communication and/or detection;

For light coupling to/from light conducting units for transmission, reflection, light scattering and absorbance measurements;

For imaging light coupling to/from microscope slide to microscope;

For coupling illuminating light to/from substrate glass and cover-glass in microscopic procedures;

For coupling light within the infrared region for efficient heating of certain details, e.g. skin portions.

The optointerface of the invention may also be used in critical-angle refractometry. Hence, light beams ranging over an angle of incidence interval and reflected within a prism or optical fibre are coupled, through the optointerface, between the prism and the exchangeable transparent liquid containing process pipe or flow cell.

Another use of the optointerface is in optical grating couplers. Hence, the optointerface may be used to couple light between a planar waveguide and an exchangeable planar waveguide or transparent plate that is provided with a grating region.

Still another use of the optointerface is in a reflection-type refractive index detector. This technique is based on coupling a light beam from a prism into a flow cell where the prism surface form one side of the flow cell. Further, the refractive index increment due to the presence of the analyte is a measurement of the light intensity reflected back into the prism from a reflective surface that forms the opposite side of a flow cell. By use of the optointerface, the light beam can be coupled between the prism and an exchangeable plane transparent plate that forms a stationary or exchangeable side of the flow cell.

The invention will now be described in more detail by way of non-limiting embodiments of the invention, reference being made to the accompanying drawings, wherein FIG. 1 is a schematic partial view of an arrangement for microscopy including an embodiment of the optical interface means, or "optointerface", according to the present invention;

Figure 1:
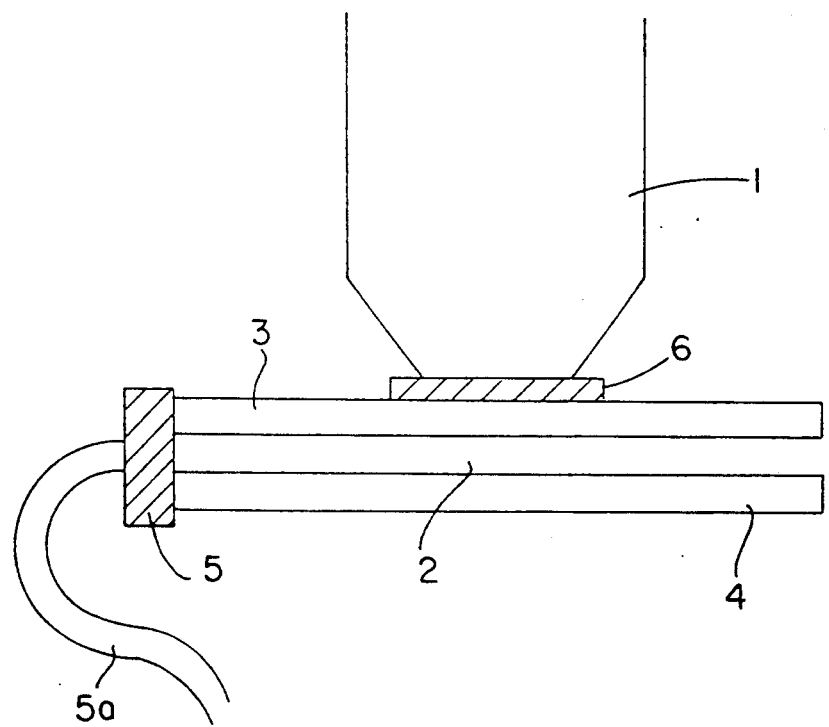

In FIG. 1 the objective lens 1 of a microscope is set for examining a specimen 2 enclosed between a coverglass 3 and a substrate glass 4. The specimen could, for example, be illuminated by an optical fibre 5a coupled through a second optointerface 5 to the specimen 2, cover- and substrate glasses 3, 4. The objective lens 1 is light coupled to the cover-glass 3 through a transparent elastic material layer or flat body 6 attached to the cover-glass 3 and brought into close, air-excluding contact with the lens 1. The cover-glass plate 3 and the transparent elastic material body 6 supported thereby thus form a reusable light coupling means or optointerface. Since the incident light in this case is normal to the contact interface between lens 1 and light-coupler 6, a moderate deviation between the refractive index of the lens 1 and that of the transparent elastic material 6 is not detrimental to the light coupling performance. The optointerface assembly 3, 6 may easily be removed and repeatedly applied to the lens 1 without any need of wiping the lens as in the case of using an immersion oil for the light coupling.

In an alternative embodiment the optointerface could include, e.g., a separate transparent plate, having opposed elastic layers of transparent material on both faces thereof. In this case the optointerface is thus a separate unit insertable between lens and cover glass plate, and it may, for example, be adapted to be fixed to the microscope by suitable means therefore.

Figure 2:
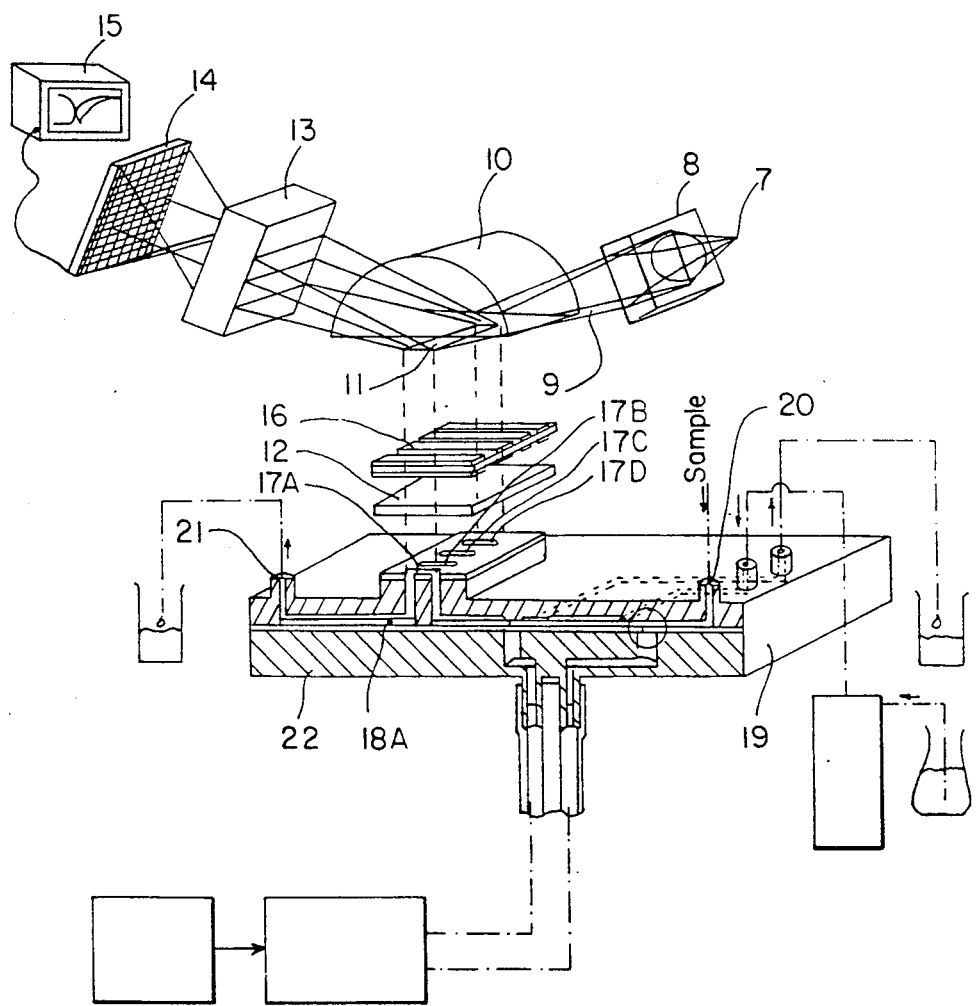
FIG. 2 is a schematic exploded view of an optical biosensor system, based upon surface plasmon resonance (SPR), including an embodiment of an optointerface according to the present invention.

FIG. 2 illustrates, in a schematical exploded view, an optical biosensor system based upon surface plasmon resonance (SPR). The system comprises a source of light 7, first lens means 8 for directing a transversely extending convergent beam 9 toward a prism 10 whereby the beam is focussed in the bottom surface of the prism to thus form a streak 11 of light. Rays of light reflected from the sensing areas of a sensor unit 12 are imaged via an anamorphic lens system 13 on a two-dimensional photodetector device 14. The electric signals created by the photodetectors are processed in an evaluation device 15 in the form of a computer. By means of the prism 10 and an optointerface 16 according to the present invention light is directed into streak 11 on the sensor unit 12 which is to lie in contact with a number of parallel, upwardly open portions 17 A-D of flow channels 18 A-D, respectively; only one of these, 18 A, is shown. The flow channels form part of a block unit 19 for liquid handling, this unit being provided with schematically indicated inlet connection means 20 and outlet connection means 21 for each of the flow channels.

Figure 3:
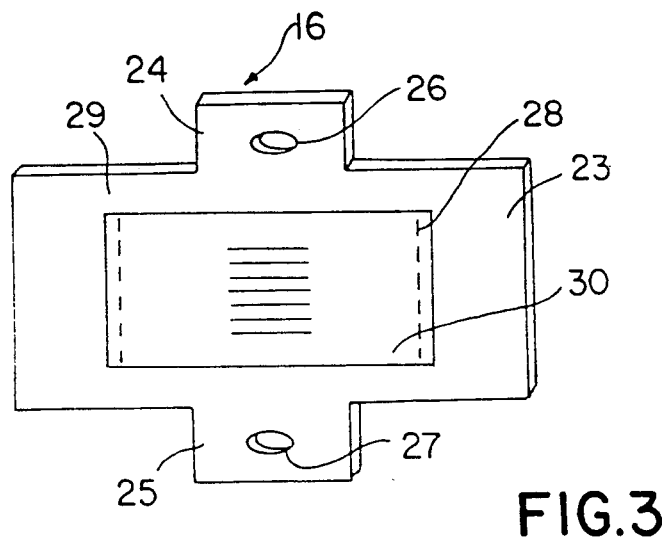
FIG. 3 is a plan view of the optointerface in FIG. 2.
Figure 4:
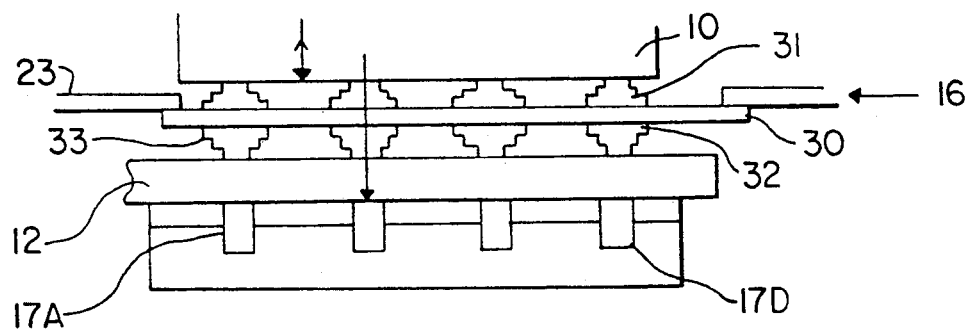
FIG. 4 is a sectional view of the optointerface of FIG. 2 coupled to the sensor unit and liquid handling block of the biosensor system in FIG. 1.

FIG. 3 shows a plan view of the more detailed design of the optointerface plate 16 in FIG. 2 and FIG. 4 shows the optointerface inserted between the prism 10 and the sensor unit 12 in FIG. 2; the sensor unit 12 contacting the liquid handling block unit 22 containing the flow channels 17 A-D. The optointerface 16 comprises a metal (or plastic) frame or holder 23 which has two projecting tongues 24, 25, said tongues being provided with one hole each, these holes 26, 27 extending all through the thickness of the tongues and serving to receive two guide pins of a housing (not shown) accommodating the light source 7, the lens means 8, the prism 10, the imaging optical unit 13 and the photodetector device 14 in fixed positions. The guide pins serve to retain the frame 23 in proper position. The frame 23 has two flanges 28, 29 against which a transparent plate 30 of glass or plastic has been applied. On one of its faces plate 30 is provided with a number of longitudinally extending parallel ridges 31 in side-by-side relationship. On its opposite face the plate has a corresponding number of parallel longitudinal ridges 32 lying opposite the ridges of the first-named plate face. The ridges are made of a transparent elastic material and spaced apart a distance corresponding to that between the upwardly open portions 17 A-D of the flow channels. As will be seen more clearly from FIG. 4 the ridges 31, 32 have longitudinally extending stepped portions 33 at each side to thus form a structure having in cross section the configuration of a flight of stairs, the uppermost step or top platform of each of these stepped structures being capable of being pressed resiliently against the sensor unit 12 and, respectively, the prism 10. This stepped configuration prevents air pockets from being formed between the interfaces contiguous to the prism and, respectively, the sensor unit. FIG. 4 shows the prism 10, the optointerface plate 16 and the sensor unit 12 in the analysis position of the biosensor apparatus in FIG. 2. Ridges 31, 32 are spaced apart in such a manner that the distances between them correspond to the distances between the upwardly open portions 17 A-D of the flow channels 18 A-D.

This arrangement of the ridges 31, 32 on the optointerface plate, the holes 26, 27 for the guide pins, corresponding holes on a carrier plate (not shown) of the sensor unit 12 and the stationary mounting of the upwardly open portions 17 A-D of the block unit for liquid handling ensure that the lower ridges 32 will serve as sources of light which lie directly above each of the corresponding channel portions 17 A-D. No scattered light from neighboring ridges 32 will interfere with the resonance angle determination for the individual sensing surfaces. In this manner it is possible to have a great number of these channel portions packed next to one another. As an example, it may be mentioned that up to 20 of such upwardly open channel portions can be packed together within a breadth of about 10 mm without any scattered light interfering with the measuring operation.

The frame or holder 23 of the optointerface 16 makes the latter easy to handle and ensures, as mentioned above, correct positioning thereof on the prism 10.

The transparent plate 30 may, e.g. be made from borosilicate glass and may, for example, be attached to the frame 23 by glueing. For the above described application a suitable thickness may be about 100 μm. The plate 30 should have at least essentially the same refractive index as the prism 10 (obliquely incident light).

Also the transparent elastic material forming the ridges 31, 32 should, of course, have essentially the same refractive index as the plate 30 and prisms 10. The elastic material may, e.g., be a silicone rubber, a polybutadiene or an epoxy resin. A silicone rubber having nearly the same refractive index as borosilicate glass ($n_e=1,52$) is that of the commercial designation Dow Corning Optigard X3-6663 Optical fiber coating ($n_e=1,51$). For the described application the ridges 31, 32 may, for example, have a length of about 7 mm, a width of about 700 μm and a height (or thickness) of about 50 μm. Instead of having the illustrated stepped configuration the ridges could be dome-shaped or the like which would likewise prevent the formation of air pockets.

An optointerface as described above may, for example, be produced by glueing a piece of glass of a suitable refractive index, thickness and size to a metallic frame and then attaching the ridges of transparent elastic material, such as silicone rubber, to the glass by moulding with moulds of a suitable material, such as metal, plastic, ceramics or silcone materials.

By providing extra ridges 31, 32 in the above described optointerface, in addition to those used for light coupling, uniform compression of as well as homogeneous environments for all the light coupling ridges may be ensured. Thus, for example, in case of a single light coupling ridge, two flanking ridges should preferably be provided.

An optointerface of the type described above may alternatively be provided with the transparent elastic material only on the glass plate side facing the sensor unit, the other side of the glass plate being attached to the prism by an immersion oil.

The invention is, of course, not limited to the embodiments specifically described above and illustrated in the drawings, but many variations and modifications are within the scope of the inventive concept as stated in the appended claims.

I claim:

1. An optical interface for repeated non-permanent passive coupling of light between two optically transparent media, at least one of these media being solid comprising:
   at least one reusable, shaped body of an optically transparent elastic material adapted to resiliently contact said solid media, said optically transparent elastic material having a refractive index matched to a refractive index of said solid media; and
   a support member for supporting said at least one reusable, shaped body;
   wherein said support member is at least partially optically transparent and said at least one reusable, shaped body is attached on at least one side to said support member to form at least one light coupling path.

2. The optical interface of claim 1, further comprising a holder member for carrying said support member.

3. The optical interface of claim 2, wherein said optically transparent media are planar substrates, such as glass.

4. The optical interface of claim 3 wherein said transparent elastic material is one of a rubber material and a cross-linked elastomer.

5. The optical interface of claim 4, wherein said transparent elastic material is a silicone rubber.

6. The optical interface of claim 5 wherein said support member is one of glass, plastic and quartz.

7. The optical interface according to any one of claims 1-6 further comprising:
   a prism;
   a sensor unit, having at least one sensing area, in internal reflection based systems to permit docking between the prism and the sensor unit; and
   a transparent plate of glass carrying on one of its faces longitudinally extending parallel ridges aligned with longitudinally extending parallel ridges on the opposite face of the plate, said longitudinally extending parallel ridges being made of an elastic transparent material, spaced apart, in the case of more than one sensing area, with distances inter se corresponding to the distances between defined sensing areas of said sensor unit, of a length at least sufficient to have the entire cross section of an incident beam of light coupled to the sensor unit, and intended for being pressed against the sensor unit directly opposite said sensing areas, to direct the light into the sensor unit.

8. The optical interface of claim 7, wherein each longitudinally extending parallel ridge on both sides of said transparent plate has a number of longitudinally extending stepped portions at each side to form a structure having in cross section the configuration of a flight of stairs, the uppermost steps thereof being capable of being pressed resiliently against the sensor unit and the prism without formation of enclosed air pockets.

* * * * *

UNITED STATES PATENT AND TRADEMARK OFFICE
CERTIFICATE OF CORRECTION

PATENT NO. : 5,164,589
DATED : November 17, 1992
INVENTOR(S) : H. Sjodin

It is certified that error appears in the above-indentified patent and that said Letters Patent is hereby corrected as shown below:

Claim 7, column 6 lines 27-46 should read as follows:

The optical interface according to any one of claims 1-6 further comprising:

a prism; and a sensor unit, having at least one sensing area, in internal reflection based systems to permit docking between the prism and the sensor unit;

wherein said support member is a transparent plate of glass carrying on one of its faces said at least one shaped body which has longitudinally extending parallel ridges aligned with longitudinally extending parallel ridges on the opposite face of the transparent plate, said longitudinally extending parallel ridges being made of said optically transparent elastic material, spaced apart, in the case of more than one sensing area, with distances inter se corresponding to the distances between defined sensing areas of said sensor

UNITED STATES PATENT AND TRADEMARK OFFICE
CERTIFICATE OF CORRECTION

PATENT NO. : 5,164,589
DATED : November 17, 1992
INVENTOR(S) : H. Sjodin

It is certified that error appears in the above-indentified patent and that said Letters Patent is hereby corrected as shown below:

unit, of a length at least sufficient to have the entire cross section of an incident beam of light coupled to the sensor unit, and intended for being pressed against the sensor unit directly opposite said sensing areas, to direct the light into the sensor unit.

Signed and Sealed this

Twenty-eighth Day of December, 1993

Attest:

BRUCE LEHMAN

Attesting Officer     Commissioner of Patents and Trademarks